US010196325B2

(12) United States Patent
Soultanidis et al.

(10) Patent No.: US 10,196,325 B2
(45) Date of Patent: Feb. 5, 2019

(54) PROCESS FOR CONVERTING SYNGAS TO AROMATICS AND CATALYST SYSTEM SUITABLE THEREFOR

(71) Applicant: ExxonMobil Chemical Patents Inc.

(72) Inventors: Nikolaos Soultanidis, Houston, TX (US); Mayank Shekhar, Houston, TX (US); John S. Coleman, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/965,099

(22) Filed: Dec. 10, 2015

(65) Prior Publication Data

US 2016/0207846 A1 Jul. 21, 2016

Related U.S. Application Data

(60) Provisional application No. 62/103,781, filed on Jan. 15, 2015.

(51) Int. Cl.
 *C07C 1/20* (2006.01)
 *C07C 27/00* (2006.01)
 (Continued)

(52) U.S. Cl.
 CPC .............. *C07C 1/20* (2013.01); *B01J 23/6562* (2013.01); *B01J 29/405* (2013.01);
 (Continued)

(58) Field of Classification Search
 CPC .................................. C07C 1/20; C07C 27/00
 (Continued)

(56) References Cited

U.S. PATENT DOCUMENTS 3,894,102 A 7/1975 Chang et al.
3,894,103 A 7/1975 Chang et al.
(Continued)

FOREIGN PATENT DOCUMENTS

CN 101602643 12/2009
CN 101602648 12/2009
(Continued)

OTHER PUBLICATIONS

U.S. Appl. No. 14/829,399, "Production of Aromatics from Methanol and Co-Feeds", Buchanan et al.
(Continued)

*Primary Examiner* — Thuan D Dang

(57) ABSTRACT

The present invention relates to a multistage process and catalyst system therefor to convert syngas to aromatics. In a first stage, syngas is converted to a $C_1$-$C_4$ alcohol mixture by contacting syngas with a first catalyst comprising rhodium or copper at moderate temperature. In a second stage, the $C_1$-$C_4$ alcohol mixture is converted into an aromatic product by contact with a second catalyst comprising a molecular sieve and at least one Group 8-14 element, the molecular sieve having a Constraint Index about 1 to 12 and a silica to alumina ratio of about 10 to 100 at effective conversion conditions. The final aromatic product is rich in benzene, toluene, and xylenes (e.g. greater than 50% aromatics on a hydrocarbon basis).

15 Claims, 1 Drawing Sheet

(51) Int. Cl.
*B01J 29/40* (2006.01)
*B01J 23/656* (2006.01)
*C07C 29/151* (2006.01)

(52) U.S. Cl.
CPC ...... *C07C 29/1518* (2013.01); *C07C 2529/40* (2013.01); *C07C 2529/65* (2013.01); *C07C 2529/70* (2013.01); *Y02P 20/52* (2015.11)

(58) Field of Classification Search
USPC .................................. 585/323, 469; 568/700
See application file for complete search history.

(56) References Cited

U.S. PATENT DOCUMENTS

| | | | |
|---|---|---|---|
| 3,894,104 A | 7/1975 | Chang et al. | |
| 3,894,107 A | 7/1975 | Butler et al. | |
| 3,941,871 A * | 3/1976 | Dwyer | B01J 29/405 423/331 |
| 4,011,275 A | 3/1977 | Zahner | |
| 4,035,430 A | 7/1977 | Dwyer et al. | |
| 4,039,600 A | 8/1977 | Chang | |
| 4,049,573 A | 9/1977 | Kaeding | |
| 4,058,576 A | 11/1977 | Chang et al. | |
| 4,076,761 A | 2/1978 | Chang et al. | |
| 4,088,706 A | 5/1978 | Kaeding | |
| 4,237,063 A | 12/1980 | Bell et al. | |
| 4,423,274 A * | 12/1983 | Daviduk | B01J 8/1809 585/640 |
| 4,628,135 A | 12/1986 | Owen et al. | |
| 4,788,369 A | 11/1988 | Marsh et al. | |
| 5,365,004 A | 11/1994 | Beck et al. | |
| 5,367,099 A | 11/1994 | Beck et al. | |
| 5,625,103 A | 4/1997 | Abichandani et al. | |
| 5,633,417 A | 5/1997 | Beck et al. | |
| 5,675,047 A | 10/1997 | Beck et al. | |
| 5,705,726 A | 1/1998 | Abichandani et al. | |
| 5,998,688 A | 12/1999 | Abichandani et al. | |
| 6,028,238 A | 2/2000 | Beck et al. | |
| 6,346,555 B1 * | 2/2002 | Luo | B01J 23/58 518/713 |
| 6,500,781 B2 | 12/2002 | Luo et al. | |
| 7,453,018 B2 | 11/2008 | Dakka et al. | |
| 7,799,962 B2 | 9/2010 | Dakka et al. | |
| 2002/0037938 A1 | 3/2002 | Luo et al. | |
| 2009/0149558 A1 * | 6/2009 | Hensley | B01D 53/04 518/722 |
| 2013/0158323 A1 * | 6/2013 | Mondal | B01J 29/40 585/408 |
| 2015/0175499 A1 | 6/2015 | Ou et al. | |

FOREIGN PATENT DOCUMENTS

| | | |
|---|---|---|
| CN | 101607864 | 12/2009 |
| CN | 101780417 | 7/2010 |
| CN | 101823929 | 9/2010 |
| EP | 0 010 295 | 4/1980 |
| EP | 0 082 701 | 6/1983 |
| GB | 1 446 522 | 8/1976 |
| WO | 2005/068406 | 7/2005 |

OTHER PUBLICATIONS

Hu et al., "Conversion of biomass-derived syngas to alcohols and $C_2$ oxygenates using supported Rh catalysts in a microchannel reactor", Catalysis Today 120 (2007) pp. 90-95.
EP Search for 2015EM002 dated Nov. 8, 2015, pp. 1-5.

* cited by examiner

PROCESS FOR CONVERTING SYNGAS TO AROMATICS AND CATALYST SYSTEM SUITABLE THEREFOR

CROSS REFERENCE TO RELATED APPLICATIONS

This application claims the benefit of priority to U.S. Provisional Application No. 62/103,781, filed Jan. 15, 2015, the disclosure of which is fully incorporated herein by reference.

FIELD OF THE DISCLOSURE

This disclosure relates to a process for converting syngas to aromatics and a catalyst system suitable therefor. In particular, the disclosure relates to a process for converting syngas to aromatics by utilizing a combination of rhodium-based or copper-based catalyst in at least one first stage conversion and zeolite catalyst in at least one second stage conversion.

BACKGROUND INFORMATION

Benzene, toluene, and xylenes (BTX) are common building blocks of modern petrochemical industries. The present source of these compounds primarily is the refining of petroleum, but alternative sources of aromatics that are independent of refining are desirable. Conversion of various feeds to aromatic compounds becomes an industrially valuable option. Some conventional methods can include conversion of methanol and/or olefins to aromatics in the presence of a molecular sieve, such as ZSM-5. Reactions for conversion of methanol and/or olefins to aromatics can be useful, for example, for creation of aromatics as individual products, or for formation of aromatic and olefin mixtures for use as naphtha boiling range or distillate boiling range fuels.

Methanol can be converted to gasoline employing the MTG (methanol to gasoline) process. The MTG process is disclosed, including, for example, U.S. Pat. Nos. 3,894,103; 3,894,104; 3,894,107; 4,035,430 and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because the $C_{10}+$ olefin precursors of the desired distillate are rapidly converted via hydrogen transfer to heavy polymethylaromatics and $C_4$ to $C_8$ isoparaffins under methanol conversion conditions.

These light aromatics are also produced in a related process for converting methanol to olefins (MTO). U.S. Pat. Nos. 4,049,573 and 4,088,706 disclose conversion of methanol to a hydrocarbon mixture rich in $C_2$-$C_3$ olefins and mononuclear aromatics, particularly para-xylene, by contacting the methanol at a temperature of 250-700° C. and a pressure of 0.2 to 30 atmospheres with a crystalline aluminosilicate zeolite catalyst which has a Constraint Index of 1-12 and which has been modified by the addition of an oxide of boron or magnesium either alone or in combination or in further combination with oxide of phosphorus. The above-identified disclosures are incorporated herein by reference.

More recently, Chinese publications CN 101602648, CN 101602643, CN 101607864, and CN 101780417 describe use of selectivated catalysts for conversion of methanol to para-xylene. According to these publications, zeolite catalysts are treated with silicate compounds, such as tetraethylorthosilicate, to provide improved selectivity for formation of olefins and para-xylene from methanol feeds. However, silicon treatment introduces several undesired effects, e.g. it reduces the per pass aromatic yield and promotes coke deposition that limits the catalyst cycle length. Especially for metal promoted zeolites, silicon treatment can promote metal migration and sintering that result to shorter catalyst lifetime.

In terms of the sources of methanol, there are various ways to produce the product through chemical reactions. For example, synthesis gas ($CO+H_2$) is readily obtained from fossil fuels and can be further converted to lower aliphatic oxygenates, especially methanol and/or dimethyl ether. U.S. Pat. No. 4,237,063 discloses the conversion of synthesis gas to oxygenated hydrocarbons using metal cyanide complexes. U.S. Pat. No. 4,011,275 discloses the conversion of synthesis gas to methanol and dimethyl ether by passing the mixture over a zinc-chromium acid or copper-zinc-alumina acid catalyst. U.S. Pat. No. 4,076,761 discloses a process for making hydrocarbons from synthesis gas wherein an intermediate product formed is a mixture of methanol and dimethyl ether.

Some processes relating to converting syngas to ethanol and $C_2+$ oxygenates are disclosed. EP 010,295A describes a process for preparing ethanol from synthesis gas, in which the reaction is carried out over a supported rhodium catalyst comprising, as co-catalyst, one or more of the elements zirconium, hafnium, lanthanum, platinum, chromium and mercury.

U.S. Pat. Nos. 6,346,555 and 6,500,781 disclose a catalyst and a process for preparing $C_2$- oxygenates by reaction of CO and $H_2$ over a rhodium-containing supported catalyst, in which the catalyst consists essentially of rhodium, zirconium, iridium, at least one metal selected from amongst copper, cobalt, nickel, manganese, iron, ruthenium and molybdenum, and at least one alkali metal or alkaline earth metal selected from amongst lithium, sodium, potassium, rubidium, magnesium and calcium, on an inert support.

However, there is an ongoing need to provide improved catalyst systems and processes for producing aromatics from various feeds, such as alcohols. An object of this disclosure is to increase the conversion of syngas to aromatics, and obtain a final aromatic product rich in benzene, toluene, and xylenes (e.g. greater than 50% aromatics on a hydrocarbon basis).

SUMMARY OF THE DISCLOSURE

The present invention relates to a multistage process and catalyst system therefor to convert syngas to aromatics. In a first stage, syngas is converted to a $C_1$-$C_4$ alcohol mixture by contacting syngas with a first catalyst comprising rhodium or copper at moderate temperature. In a second stage, the $C_1$-$C_4$ alcohol mixture is converted into an aromatic product by contact with a second catalyst comprising a molecular sieve and at least one Group 8-14 element, the molecular sieve having a Constraint Index about 1 to 12 and a silica to alumina ratio of about 10 to 100 at effective conversion conditions. The final aromatic product is rich in benzene, toluene, and xylenes (e.g. greater than 50% aromatics on a hydrocarbon basis).

DETAILED DISCLOSURE

Figure 1:
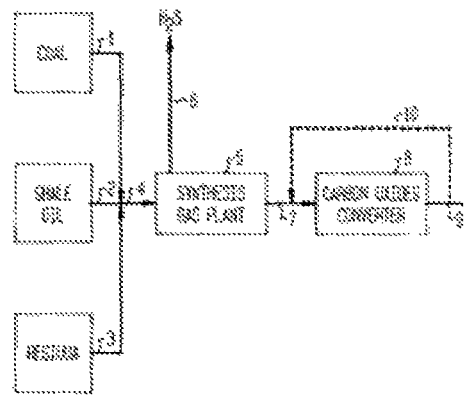
FIG. 1 is a process flow sheet describing a conversion technique according to the present disclosure.

The present invention relates to a multistage process and catalyst system therefor to convert syngas to aromatics. In a first stage, syngas is converted to a $C_1$-$C_4$ alcohol mixture by contacting syngas with a first rhodium-based or copper-based catalyst at moderate temperature; then the $C_1$-$C_4$ alcohol mixture, directly feeding as a feedstock to a second stage, is converted into aromatics by contact with a second catalyst comprising a molecular sieve, having a Constraint Index about 1 to 12 and a silica to alumina ratio of about 10 to 100, and at least one Group 8-14 element at effective conversion conditions. The second catalyst may also be modified with phosphorous.

The combination of the inventive catalyst system and effective conversion conditions can allow for an improved yield aromatics compared to the one-step conversion process of syngas to aromatics and the conversion of methanol to aromatics; reduced production of less desirable side products, such as methane, CO, $CO_2$, and/or coke; or a combination thereof. In addition, conversion of $C_2$+ alcohols to aromatics is considerably less exothermic compared to methanol conversion to aromatics. The present disclosure using a $C_1$-$C_4$ alcohol mixture as feed in the second stage would lessen the amount of heat that is required to be removed from the reactors than a methanol feed.

Without being bound by any theory, it is believed that the inventive process and catalyst system improves the production of aromatics primarily due to the ethanol dehydration reaction by ethylene aromatization. The presence of ethanol and other $C_3$-$C_4$ aliphatic alcohols promotes the formation and stabilization of reactive intermediate species. These ethanol derived species convert more easily to aromatics opposite to methanol intermediates that can undergo side-reactions that form unwanted byproducts.

Formation of Synthesis Gas

Synthesis gas and syngas are used interchangeably in the context of the present disclosure. For the first stage conversion, any hydrocarbon-containing feed stream that can be converted into a feedstock comprising carbon monoxide and hydrogen, most preferably a synthesis gas, is useful in the processes of the disclosure. The volume ratio of hydrogen to carbon monoxide ($H_2$:CO) in the reaction zone is preferably in the range of 20:1 to 0.1:1, more preferably in the range of 5:1 to 1:1, most preferably in the range of 2.5:1 to 1.5:1, e.g. 2:1. Useful feed streams include natural gas (mainly methane, but natural gas composition can vary depending on location and source), naphtha, refinery off-gas, liquefied petroleum gas (LPG), gas oil, vacuum residuals, shale oils, asphalts, various types of fuel oils, coal based/lignin deposits, hydrocarbon containing process recycle streams and biomass derived gas. According to one preferred embodiment of the present disclosure, methane is used as the hydrocarbon-containing feed stream to be converted into CO and $H_2$.

Processes for producing mixtures of carbon monoxide and hydrogen (synthesis gas) have its advantages and disadvantages and the choice of using a particular reforming process is dictated by economic and available feed stream considerations, as well as by the desired mole ratio of $H_2$:CO in the feedstock resulting from the reforming reaction. The synthesis gas may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof a discussion of these synthesis gas production technologies is provided in *Hydrocarbon Processing*, V78, No. 4, 87-90, 92-93 (April 1999) and *Petrole et Techniques*, No. 415, 86-93 (July-August 1998). It is also envisaged that the synthesis gas may be obtained by catalytic partial oxidation of hydrocarbons in a microstructured reactor as exemplified in *IMRET 3: Proceedings of the Third International Conference on Microreaction Technology*, Editor W. Ehrfeld, Springer Verlag, 1999, pages 187-196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in *Hydrocarbon Engineering*, 2000, 5, (5), 67-69; *Hydrocarbon Processing*, 79/9, 34 (September 2000); *Today's Refinery*, 15/8, 9 (August 2000); WO 99/02254; and WO 200023689.

Synthesis gas may undergo treatment and reduce in carbon dioxide content prior to being fed to the first reaction zone. For use in the processes of this disclosure, the synthesis gas should preferably be essentially free of catalyst poisons and inhibitors such as hydrogen sulfide, carbonyl sulfide, metal carbonyls, e.g. iron carbonyl and nickel carbonyl, ammonia, basic organic compounds, e.g. methyl amine and ethyl amine, and generally any compounds that will neutralize an acid. Synthesis gas treatment may be carried out by processes known in the art. See, for example, Weissermel, K. and Arpe H.-J., *Industrial Organic Chemistry*, Second, Revised and Extended Edition, 1993, pp. 19-21.

First Stage Catalyst

The first catalyst for conversion of syngas to a $C_1$-$C_4$ alcohol mixture comprises rhodium or copper. Rhodium is the preferred metal catalyst employed in the first stage of the process, as rhodium (Rh) appears to be one of more adaptable elements in the transition series in terms of its properties for catalysis, particularly for syngas conversion. A rhodium catalyst on silica and/or vanadium tends to yield alcohol synthesis with high selectivity towards ethanol. The rhodium-based catalyst used in the present disclosure is preferably a rhodium-based catalyst supported on silica, such as Rh—Mn/$SiO_2$.

Preferably, the rhodium-based catalyst used in the present disclosure is a rhodium-based catalyst consisting of components Rh—Mn—Fe—$M_1$-$M_2$ supported on silica, wherein $M_1$ can be Li and/or Na, and $M_2$ can be Ru and/or Ir, wherein Rh is 0.1 to 3%, preferably 0.3 to 2%, by weight based on the total catalyst weight and the weight ratio of Mn/Rh is 0.5-12, the weight ratio of Fe/Rh is 0.01-0.5, the weight ratio of $M_1$/Rh is 0.04-0.2, and the weight ratio of $M_2$/Rh is 0.1-1.0.

The metal catalysts can be employed in said first stage conversion also include those compounds containing copper, e.g. Cu—Cs, Cu—Co—Zn, Cu—Zn—Fe, Cu—Co—Zn—Fe, Cu—Co—Zn—Fe—Ca, Cu—Co—Zn—Mo—Na and Cu—Co—Zn—Fe. The catalyst may be prepared by adding a solution of $(NH_4)_2CO_3$ dissolved in distilled water to a solution of at least one metallic compound selected from the group consisting of $Zn(OAc)_2.H_2O$, $Co(OAc)_3.H_2O$, $Cu(OAc)_2.H_2O$, $Fe(NO_3)_3.9H_2O$, $(NH_4)_6Mo_7O_{24}.4H_2O$, $Ca(NO_3)_2.4H_2O$, NaOH, $K_2PtCl_4$, $PdCl_2$, $HrCl_3$, $RuCl_3$, $NiCl_2$, $CrCl_3$, $WCl_3$, $OsCl_3$, and $AlCl_3$, drying the result mixture at a temperature of about 120° C. overnight and calcining the dried material at a temperature of about 450°

C. and for a period of about 16 hours. The metallic compound may be employed in an amount ranging from 0.01 to 95 wt %, more preferably from 0.1 to 80 wt % and most preferably from 1 to 50 wt %.

Second Stage Catalyst

The catalyst used in the second stage conversion of the $C_1$-$C_4$ alcohol mixture to aromatics comprises a molecular sieve and at least one Group 8-14 element. The catalyst can optionally further comprise phosphorus and/or lanthanum and/or other elements from Group 1-2 and/or Group 13-16 of the Periodic Table that provide structural stabilization. In this sense, the term "comprising" can also mean that the catalyst can comprise the physical or chemical reaction product of the molecular sieve and the Group 8-14 element or combination of elements from the same group (and optionally phosphorus and/or lanthanum and/or other elements from groups 1-2 and/or group 13-16). Optionally, the catalyst may also include a filler or binder and may be combined with a carrier to form slurry.

In this description, reference to a group number for an element corresponds to the current IUPAC numbering scheme for the periodic table. One or more Group 8-9 element (e.g., Fe, Ru, Os, Co, Rh, and Ir) may also be used. Group 10 elements (Ni, Pd, and Pt) are less commonly used in applications for forming olefins and aromatics, as the combination of a Group 10 element in the presence of hydrogen can tend to result in saturation of aromatics and/or olefins. One or more Group 11 and/or Group 12 elements (e.g., Cu, Ag, Au, Zn, and Cd) may be used. In other embodiments, one or more Group 13 elements (B, Al, Ga, In, and Tl) and/or Group 14 elements (Si, Ge, Sn, and Pb) may be used. In a preferred embodiment, the metal is selected from the group consisting of Zn, Ga, Cd, Ag, Cu, P, La, or combinations thereof. In another preferred embodiment, the metal is Zn, Ga, Ag, or a combination thereof. In particular embodiments, one or more Group 1 elements (e.g., Li, Na, K, Rb, Cs, and Fr) and/or Group 2 elements (e.g., Be, Mg, Ca, Sr, Ba, and Ra) and/or phosphorous and/or Lanthanum may be used for structural stabilization.

The molecular sieve can be modified by the Group 8-14 metal(s) in any convenient manner Typical methods for modifying a catalyst with a metal include impregnation (such as by incipient wetness), ion exchange, deposition by precipitation, and any other convenient method for depositing a metal that is supported by a catalyst and/or a catalyst support.

The molecular sieve comprises ≥10.0 wt. % of the catalyst, preferably about 40 to 100 wt. %, more preferably about 60 to 100 wt. %, and most preferably about 80 to 100 wt. %, the weight percent excluding any binder that may be used. As used herein the term "molecular sieve" refers to crystalline or non-crystalline materials having a porous structure. Microporous molecular sieves typically have pores having a diameter of ≤about 2.0 nm Mesoporous molecular sieves typically have pores with diameters of about 2 to about 50 nm Macroporous molecular sieves have pore diameters of >50.0 nm. The pore diameter of the molecular sieve used is preferably about 0.1 to 50 nm, more preferably 0.1 to 25 nm, and most preferably 0.1 to 10 nm.

Additionally or alternatively, some molecular sieves useful herein are described by a Constraint Index of about 1 to about 12. Constraint Index is determined as described in U.S. Pat. No. 4,016,218, incorporated herein by reference for details of the method.

Particular molecular sieves are zeolitic materials. Zeolitic materials are crystalline or para-crystalline materials. Some zeolites are aluminosilicates comprising [$SiO_4$] and [$AlO_4$] units. Other zeolites are aluminophosphates (AlPO) having structures comprising [$AlO_4$] and [$PO_4$] units. Still other zeolites are silicoaluminophosphates (SAPO) comprising [$SiO_4$], [$AlO_4$], and [$PO_4$] units.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

Additionally or alternatively, the molecular sieves useful herein may be characterized by a ratio of Si to Al. In particular embodiments, the molecular sieves suitable herein include those having a Si/Al ratio of about 10 to 100, preferably about 10 to 80, more preferably about 20 to 60, and most preferably about 20 to 40.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference.

Particular molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-34 (U.S. Pat. No. 4,079,095) ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780), more preferably is ZSM-5. The entire contents of the above references are incorporated by reference herein. Other useful molecular sieves include MCM-22, PSH-3, SSZ-25, MCM-36, MCM-49 or MCM-56, with MCM-22. Still other molecular sieves include Zeolite T, ZKS, erionite, and chabazite.

Another option for characterizing a zeolite (or other molecular sieve) is based on the nature of the ring channels in the zeolite. The ring channels in a zeolite can be defined based on the number of atoms including in the ring structure that forms the channel. In some aspects, a zeolite can include at least one ring channel based on a 10-member ring. In such aspects, the zeolite preferably does not have any ring channels based on a ring larger than a 10-member ring. Examples of suitable framework structures having a 10-member ring channel but not having a larger size ring channel include EUO, PER, IMF, LAU, MEL, MFI, MFS, MTT, MWW, NES, PON, SFG, STF, STI, TON, TUN, MRE, and PON.

The catalyst also includes at least one metal selected from Group 8-14 of the Periodic Table, such as at least two metals (i.e., bimetallic) or at least three metals (i.e., trimetallic). Typically, the total weight of the Group 8-14 elements is ≥0.1 wt. % and ≤about 20.0 wt. %, preferably about 1 to 20.0 wt. %, more preferably about 1 to 10.0 wt. %, and most preferably about 1 to 5 wt. %, the weight percent excluding any binder that may be used. Of course, the total weight of the Group 8-14 elements shall not include amounts attributable to the molecular sieve itself or any binder that is used.

Additionally or alternatively, in some aspects, the catalyst can also include at least one of phosphorous and/or lanthanum and/or other elements from groups 1-2 and/or group 13-16, such as at least two such elements or at least three such elements. Typically, the total weight of the phosphorous and/or lanthanum and/or other elements from groups 1-2 and/or groups 13-16 is ≥0.1 wt. %≤about 10.0 wt. %, based on the total weight of the catalyst. Of course, the total weight of the phosphorous and/or lanthanum and/or other elements from Groups 1-2 and/or Groups 13-16 shall not include amounts attributable to the molecular sieve itself.

Particular molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ElAPSO where El is Be, B, Cr, Co, Ga, Fe, Mg, Mn, Ti, or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO), EP-A-0 161 489 (CoAPSO), EP-A-0 158 976 (ELAPO, where EL is Co, Fe, Mg, Mn, Ti, or Zn), U.S. Pat. No. 4,310,440 (AlPO4), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326, and 5,478,787 (MgAPSO), U.S. Pat. No. 4,554,143 (FeAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500,651, 4,551,236, and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference.

In a preferred embodiment, the molecular sieve is a ZSM-5 based molecular sieve. In some preferred aspects, the Group 8-14 element can be selected from Groups 11-13, such as Zn, Ga, Ag, or combinations thereof. In other aspects, the Group 8-14 element can be two or more elements from Groups 11-13, such as two or more elements from the same group in Groups 11-13. In still other aspects, the molecular sieve can be modified with at least one element from Groups 8-14, such as at least two elements or at least three elements from Groups 8-14, the at least two elements or at least three elements optionally being from the same group in Groups 8-14. In any of the above aspects, a catalyst comprising a molecular sieve can be further modified by an element from Groups 1-2, Groups 13-16, lanthanum, and/or phosphorus. In a preferred embodiment, the molecular sieve is ZSM-5 and the element is Zn.

Where the catalyst composition is prepared by using a metal compound which ionizes in aqueous solution, for example, gallium nitrate, it is inevitable that some of the metal ions will be exchanged with the cations in the zeolite even if the preparation was directed to impregnation of the zeolite.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), International Patent Application WO 01/36329 published May 25, 2001 (surfactant synthesis), International Patent Application WO 01/25151 published Apr. 12, 2001 (staged acid addition), International Patent Application WO 01/60746 published Aug. 23, 2001 (silicon oil), U.S. Patent Application Publication No. 2002-0055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 2002-0115897 published Aug. 22, 2002 (freeze drying the molecular sieve), which are all herein incorporated by reference in their entirety.

The catalyst employed in the present process optionally includes a binder or matrix materials that are mechanically robust, minimize attrition of the bound catalyst, resistant to the temperatures and other conditions employed in the process in addition to the materials previously discussed. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst.

Naturally occurring clays which can be utilized in the present catalyst include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. It will be recognized that the specific clay used and treatment thereof will affect performance to some extent, and the determination of the most appropriate clay (or binder more generally) is within the skill of the ordinary artisan in possession of the present disclosure to determine by routine experimentation.

In addition to the foregoing materials, the ZSM-5 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

Conversion of Syngas to Aromatics

According to one preferred embodiment of the present disclosure, syngas comprising desired molar ratio of $H_2$:CO (i.e., preferably in the range of 20:1 to 0.1:1) is fed to a first stage conversion reactor at a controlled rate and the reaction is carried out in a reaction zone under certain temperature and pressure in the presence of rhodium-based catalyst or copper-based catalyst to convert the feedstock syngas into $C_1$-$C_4$ alcohol mixture. The temperature in the first reaction zone is selected from the range of about 150° C. to 400° C., preferably a temperature in the range of about 260° C. to 300° C. The gas hourly space velocity (GHSV) of the feedstock (liters of feedstock/hour/liter of catalyst) passing through the reaction zone can vary significantly, depending upon a variety of factors such as, for example, reaction conditions, composition of the feedstock and quantity and type of catalyst being used. The GHSV can be maintained at any rate in the range of from about 1 to 30,000 $hr^{-1}$ or more, preferably will be maintained at a rate of at least about 500 $hr^{-1}$, and more preferably will be maintained at a rate of at least 1,000 $hr^{-1}$. The pressure in the conversion reaction zone may be selected from the range of 1 to 7 MPaa, preferably a pressure in the range of 2 to 5.4 MPaa. The hydrogen and carbon monoxide partial pressures should be sufficient to enable the production of a methanol, ethanol and propanol mixture.

The $C_1$-$C_4$ alcohol mixture produced in the first stage conversion includes methanol, ethanol and propanol, and also includes some other kinds of $C_2$-oxygenates, such as acetaldehyde and acetic acid. In certain embodiments, the first stage conversion yields at least 50% by weight, preferably at least 55% by weight, more preferably at least 60% by weight, of the $C_1$-$C_4$ alcohol mixture. Preferably, the $C_1$-$C_4$ alcohol mixture contains at least 10% by weight of a methanol, ethanol and propanol mixture, more preferably at least 20% by weight, most preferably at least 30% by weight, and the methanol, ethanol and propanol mixture contains at least 50% by weight of ethanol and propanol, preferably at least 55% by weight, more preferably at least 60% by weight.

In a preferred embodiment, the $C_1$-$C_4$ alcohol mixture obtained from the first stage conversion is fed to a second stage conversion reactor without further treatment at a controlled rate and the reaction is carried out in a reaction zone under certain temperature and pressure in the presence of the second catalyst to convert the feedstock into aromatics. The temperature in the second reaction zone is selected from the range of about 250° C. to 600° C., preferably a temperature in the range of about 350° C. to 450° C. The weight hourly space velocity (WHSV) of the feedstock passing through the second reaction zone can vary significantly, depending upon a variety of factors such as, for example, reaction conditions, composition of the feedstock and quantity and type of catalyst being used. The WHSV can be maintained in the range of from about 0.1 to 20. The pressure in the second reaction zone may be selected from the range of 0.1 to 2.8 MPaa, preferably a pressure in the range of 0.3 to 2.1 MPaa.

Preferably the aromatic product obtained in the second stage conversion contains at least 50% by weight of benzene, toluene and xylene product on a hydrocarbon basis, and the benzene, toluene and xylene product contains at least 20% by weight of xylenes, preferably at least 30% by weight, and most preferably at least 40% by weight on a hydrocarbon basis.

FIG. 1 illustrates one embodiment of the inventive process. Hydrocarbon-containing feed stream, such as coal, shale oil, or residua, or a combination thereof, is conveyed via line 1, 2 and 3, respectively and then via line 4 to synthesis gas plant 5, where it is converted to synthesis gas. If hydrogen sulfide is produced in a plant, it may be separated and sent via line 6 to a treatment plant (not shown) for sulfur recovery. Synthesis gas, previously treated in a catalytic carbon monoxide shift converter and then reduced in carbon dioxide content by selective sorption, is conveyed via line 7 to the first reaction zone 8 (carbon oxides converter), where it is at least partially converted through contacting the first catalyst, a rhodium-based catalyst or copper-based catalyst, to produce $C_1$-$C_4$ alcohol mixture. Part or all of the unconverted synthesis gas may be separated from such reduction product and recycled via line 10.

Figure 2:
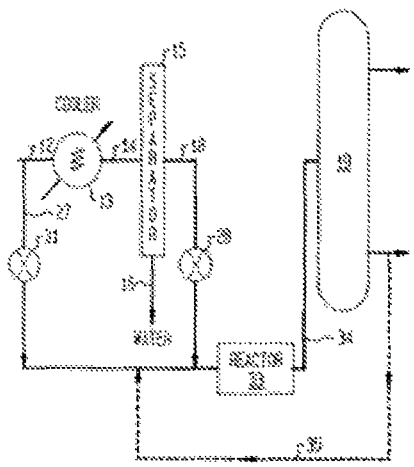
FIG. 2 is a second process flow sheet describing a conversion technique according to the present disclosure.

With reference to FIG. 2, the reaction products from the first reaction zone 8 (shown in FIG. 1) can then be diverted through line 27 and valve 31 to reactor 33 (the second reaction zone) where it is contacted with the second catalyst for conversion to aromatics rich in BTX. Optionally, the reaction products in line 12 are conveyed via line 12 to a cooler 13, and the cooled products are then conveyed via line 14 to a separator 15, which may be one integral unit. The liquid product, comprising $C_4$ to $C_9$ aliphatics, is conveyed via line 18 to reactor 33 where it is contacted with the second catalyst for conversion to aromatics rich in BTX.

The effluent stream from the reactor 33 can then pass through a separator 19 through line 34 where the reactor effluent can be quenched to facilitate separation of the effluent. The quench can be sufficient to allow removal of water from the effluent as a liquid. Light organics containing 4 carbons or less are removed as a gas phase stream. Ethylene and propylene can subsequently be separated from this light ends stream. The remaining portion of the effluent can substantially correspond to hydrocarbons that are liquids at standard temperature and pressure. A series of separations can then be performed to separate out desired products. The present invention further comprises separating at least a portion of the liquid effluent to form a $C_8$ product stream and one or more of a $C_7-$ stream and a $C_9+$ stream.

For example, a first separation on the liquid effluent can separate $C_7-$ (lower boiling) compounds from $C_8+$ (higher boiling) compounds. In the first separation, para-xylene and other $C_8+$ molecules are included in the higher boiling fraction, while $C_7-$ compounds (benzene, toluene) and other lower boiling compounds such as oxygenates form the lower boiling fraction. In this discussion, a $C_7-$ product stream is defined as a product stream where at least 50 wt % of the hydrocarbons corresponds to hydrocarbons having 7 carbons or less. Similarly, a $C_8+$ product stream is defined as a product stream where at least 50 wt % of the hydrocarbons corresponds to hydrocarbons having at least 8 carbons. This lower boiling fraction may also contain a variety of non-aromatic compounds. The lower boiling compounds from this first separation are one suitable source, if desired, for a recycle stream to provide hydrogen-lean molecules to the conversion reaction.

The $C_8+$ fraction can then be further separated into a $C_8$ fraction and a $C_9+$ fraction. The $C_9+$ fraction will typically be aromatics and is another suitable fraction for recycle, if desired. In this discussion, a $C_8$ product stream is defined as a product stream where at least 50 wt % of the hydrocarbons corresponds to hydrocarbons having 8 carbons. Similarly, a $C_9+$ product stream is defined as a product stream where at least 50 wt % of the hydrocarbons corresponds to hydrocarbons having at least 9 carbons. In some aspects, if a distillation column is used, the first separation and second separation can be combined to form the $C_7-$, $C_8$, and $C_9+$ fractions in a single distillation or fractionation process. In some aspects, the separations to form the $C_7-$, $C_8$, and $C_9+$ fractions can correspond to any convenient number of distillation steps in order to improve recovery of the desired $C_8$ fraction.

The present invention further comprises separating the $C_8$ product stream to form at least a para-xylene product stream, the para-xylene product stream having a higher concentration of para-xylene than the $C_8$ product stream. The $C_8$ fraction of the liquid effluent from conversion will typically include at least a portion of xylene isomers other than para-xylene. The ortho- and meta-xylene isomers can be separated from the para-xylene isomers by any convenient method, such as by using crystallization to separate the isomers or by selective adsorption. Optionally, the $C_8$ fraction can be treated in a xylene isomerization unit prior to recovery of the para-xylene. This can increase the concentration of para-xylene in the $C_8$ fraction relative to the concentration prior to the xylene isomerization. Optionally, the separated ortho- and meta-xylenes can be recycled back to the distillation step(s) for further recovery of any remaining para-xylene and/or for further isomerization to form more para-xylene.

The feedstock can be exposed to the conversion catalysts in the first stage conversion and/or the second stage conversion in any convenient type of reactor. Suitable reactor configurations include fixed bed reactors, fluidized bed reactors (such as ebullating bed reactors), riser reactors, and other types of reactors where the feed can be exposed to the catalyst in a controlled manner.

Having described the process and catalyst system and its various features, described herein in numbered embodiments is:

Embodiment 1

A multistage process for converting syngas to aromatics comprising: (a) contacting syngas with a first catalyst comprising rhodium or copper to produce a $C_1$-$C_4$ alcohol mixture; and (b) contacting said $C_1$-$C_4$ alcohol mixture with a second catalyst comprising a molecular sieve and at least one Group 8-14 element to produce an aromatic product, wherein said molecular sieve is characterized by a Constraint Index about 1 to 12 and silica to alumina ratio of about 10 to 100.

Embodiment 2

The process of Embodiment 1, wherein the reaction of syngas with the first catalyst in step (a) to produce said $C_1$-$C_4$ alcohol mixture has a yield of at least 50%.

Embodiment 3

The process of Embodiment 1 or Embodiment 2, wherein said $C_1$-$C_4$ alcohol mixture contains at least 10% by weight of a methanol, ethanol and propanol mixture.

Embodiment 4

The process of Embodiment 3, wherein said methanol, ethanol and propanol mixture contains at least 50% by weight of ethanol and propanol.

Embodiment 5

The process of any one of Embodiments 1-4, wherein said syngas has a volume ratio of hydrogen to carbon monoxide of 20:1 to 0.1:1.

Embodiment 6

The process of any one of Embodiments 1-5, wherein said first catalyst comprises Rh—Mn/$SiO_2$.

Embodiment 7

The process of any one of Embodiments 1-6, wherein step (a) is carried out at a reaction temperature of 260 to 300° C.

Embodiment 8

The process of any one of Embodiments 1-7, wherein said aromatic product contains at least 50% by weight of a benzene, toluene and xylene mixture on a hydrocarbon basis.

Embodiment 9

The process of Embodiment 8, wherein said benzene, toluene and xylene mixture contains at least 20% by weight of xylenes on a hydrocarbon basis.

Embodiment 10

The process of any one of Embodiments 1-9, wherein said molecular sieve is selected from the group consisting of ZSM-5, ZSM-11, ZSM-12, ZSM-22, ZSM-23, ZSM-34, ZSM-35, ZSM-48, ZSM-57 and ZSM-58.

Embodiment 11

The process of Embodiment 10, wherein said second catalyst is Zn/ZSM-5.

Embodiment 12

The process of any one of Embodiments 1-11, wherein step (b) is carried out at a reaction temperature of 250 to 600° C.

Embodiment 13

The process of Embodiment 12, wherein step (b) is carried out at a reaction temperature of 350 to 450° C.

Embodiment 14

The process of any one of Embodiments 1-13, wherein step (b) is carried out at a reaction pressure of 0.1 to 2.8 MPaa.

Embodiment 15

The process of any one of Embodiments 1-14, wherein step (b) is carried out at a weight hourly space velocity of 0.1 to 20.

Embodiment 16

The process of any one of Embodiments 1-15, further comprising separating at least a portion of said aromatic product to form a $C_8$ product stream and at least one of a $C_7$- stream and a $C_9$+ stream.

Embodiment 17

A catalyst system for converting syngas to aromatics, which comprises a first catalyst comprising rhodium or copper to convert syngas to $C_1$-$C_4$ alcohol mixture, and a second catalyst comprising a molecular sieve and at least one Group 8-14 element to produce an aromatic product, wherein said molecular sieve is characterized by a Constraint Index about 1 to 12 and silica to alumina ratio of about 10 to 100.

Embodiment 18

The catalyst system of Embodiment 17, wherein the reaction of syngas with the first catalyst in step (a) to produce said $C_1$-$C_4$ alcohol mixture has a yield of at least 50%.

Embodiment 19

The catalyst system of Embodiment 17 or Embodiment 18, wherein said $C_1$-$C_4$ alcohol mixture contains at least 10% by weight of a methanol, ethanol and propanol mixture.

Embodiment 20

The catalyst system of Embodiment 19, wherein said methanol, ethanol and propanol mixture contains at least 50% by weight of ethanol and propanol.

Embodiment 21

The catalyst system of any one of Embodiments 17-20, wherein said first catalyst is Rh—Mn/$SiO_2$.

Embodiment 22

The catalyst system of any one of Embodiments 17-21, wherein said aromatic product contains at least 50% by weight of a benzene, toluene and xylene mixture on a hydrocarbon basis.

Embodiment 23

The catalyst system of Embodiment 22, wherein said benzene, toluene and xylene mixture contains at least 20% by weight of xylenes on a hydrocarbon basis.

Embodiment 24

The catalyst system of any one of Embodiments 17-23, wherein said molecular sieve is selected from the group consisting of ZSM-5, ZSM-11, ZSM-12, ZSM-22, ZSM-23, ZSM-34, ZSM-35, ZSM-48, ZSM-57 and ZSM-58.

Embodiment 25

The catalyst system of Embodiment 24, wherein said second catalyst is Zn/ZSM-5.

The following examples will serve to illustrate the processes and merits of the present disclosure. It is to be understood that these examples are merely illustrative in nature and that the present process is not necessarily limited thereto.

Example I

The first catalyst for the first stage conversion is prepared by pre-calcinating $SiO_2$ in air at 550° C. A rhodium nitrate solution containing 10% Rh metal was used as precursor. $Mn(NO_3)_2$ was used as precursor for Manganese. Rh—Mn/ $SiO_2$ catalyst was prepared by co-impregnating Rh and Mn precursors on $SiO_2$ support. Final concentration of Rh and Mn were controlled at level of 6 and 1.5 wt %, respectively. After impregnation, the catalyst was subject to air calcination at 350° C. for 3 hours.

Example II

The second stage catalyst comprises (1) Gallium and Zinc mixed metal oxides; and (2) H-ZSM-5 zeolite with a $SiO_2$/ $AlO_2$ molar ratio of 70. The Ga and Zn mixed metal oxides were prepared by co-precipitation of $Ga(NO_3)_3$ and $Zn(NO_3)_2$ with $NH_4OH$. 4.62 g of $Cr(NO_3)_3$ and 13.41 g of $Zn(NO_3)_2$ were dissolved in 100 ml distilled water separately. The two solutions were then mixed together. $NH_4OH$ was slowly added into the mixed solution with stirring until the pH value of the solution reached about 8. The precipitate was filtered and recovered. This precipitate was dried at a temperature of 120° C. for 12 hours, and then calcined in air at 500° C. for 6 hours. These Ga/Zn mixed metal oxides were ground into powders.

The catalyst can also be prepared by physically mixing powders of a composition of 50% (w/w) Ga/Zn mixed metal oxides and 50% (w/w) H-ZSM-5 zeolite. Powders of 2.0 g of Ga/Zn mixed metal oxides and 2.0 g of H-ZSM-5 zeolite were mixed thoroughly in a grinding mortar. The mixed catalyst powders were pelletized and screened to 8-12 mesh (0.27-0.17 cm) particles.

The foregoing description of the embodiments has been provided for purpose of illustration and description. It is not intended to be exhaustive or to limit the disclosure. Individual elements or features of a particular embodiment are generally not limited to that particular embodiment, abut, where applicable, are interchangeable and can be used in a selected embodiment, even if not specifically shown or described. The same may also be varied in many ways. Such variation is not to be regarded as a departure from the disclosure, and all such modifications are intended to be included within the scope of the disclosure.

What is claimed is:

1. A multistage process for converting syngas to aromatics comprising:
    (a) contacting syngas in a first reactor with a first catalyst comprising rhodium or copper to produce a C1-C4 alcohol mixture at a gas hourly space velocity (GHSV) of at least 500 hr$^1$, wherein the GHSV is the liters of syngas per hour flowing through the first reactor divided by the liters of the first catalyst within the first reactor; and
    (b) contacting said C1-C4 alcohol mixture in a second reactor with a second catalyst comprising a molecular sieve to produce an aromatic product, wherein said molecular sieve is a ZSM-5 zeolite having a silica to alumina ratio of about 10 to 100, and wherein the second catalyst comprises said ZSM-5 zeolite physically mixed with gallium and zinc substantially in the form of mixed oxides thereof.

2. The process of claim 1, wherein the reaction of syngas with the first catalyst in step (a) to produce said $C_1$-$C_4$ alcohol mixture has a yield of at least 50%.

3. The process of claim 1, wherein said $C_1$-$C_4$ alcohol mixture contains at least 10% by weight of a methanol, ethanol and propanol mixture.

4. The process of claim 3, wherein said methanol, ethanol and propanol mixture contains at least 50% by weight of ethanol and propanol.

5. The process of claim 1, wherein said syngas has a volume ratio of hydrogen to carbon monoxide of 20:1 to 0.1:1.

6. The process of claim 1, wherein said first catalyst comprises Rh—Mn/$SiO_2$.

7. The process of claim 1, wherein step (a) is carried out at a reaction temperature of 260 to 300° C.

8. The process of claim 1, wherein said aromatic product contains at least 50% by weight of a benzene, toluene and xylene mixture on a hydrocarbon basis.

9. The process of claim 8, wherein said benzene, toluene and xylene mixture contains at least 20% by weight of xylenes on a hydrocarbon basis.

10. The process of claim 1, wherein step (b) is carried out at a reaction temperature of 350 to 450° C.

11. The process of claim 1, wherein step (b) is carried out at a reaction pressure of 0.1 to 2.8 MPaa.

12. The process of claim 1, wherein step (b) is carried out at a weight hourly space velocity of 0.1 to 20.

13. The process of claim 1, further comprising separating at least a portion of said aromatic product to form a $C_8$ product stream and at least one of a $C_{7-}$ stream and a $C_{9+}$ stream.

14. The process of claim 1, wherein the first catalyst comprises Rhodium (Rh), Manganese (Mn), Iron (Fe), $M_1$, and $M_2$, wherein $M_1$ comprises one or both of Lithium (Li) and Sodium (Na), and wherein $M_2$ comprises one or both of Ruthenium (Ru) and Iridium (Ir).

15. The process of claim 14, wherein the first catalyst comprises 0.1 to 3 wt. % Rh, and wherein:
the weight ratio of Mn/Rh in the first catalyst is 0.5-12;
the weight ratio of Fe/Rh in the first catalyst is 0.01-0.5;
the weight ratio of $M_1$/Rh in the first catalyst is 0.04-0.2; and
the weight ratio of $M_2$/Rh in the first catalyst is 0.1-1.0.

* * * * *